United States Patent [19]

Miller et al.

[11] Patent Number: 5,178,999
[45] Date of Patent: Jan. 12, 1993

[54] EPSTEIN-BARR VIRUS TRANSFORMED CELL LINES SUPERINFECTED WITH A SECOND VIRUS

[75] Inventors: George Miller; Karen E. Dahl, both of New Haven, Conn.

[73] Assignee: Yale University, New Haven, Conn.

[21] Appl. No.: 187,794

[22] Filed: Apr. 29, 1988

[51] Int. Cl.$^5$ ............... C12Q 1/00; C12Q 1/70; G01N 33/53; C12N 5/00; C12N 1/00

[52] U.S. Cl. ............................... 435/7.1; 435/5; 435/7.2; 435/7.21; 435/7.24; 435/240.2; 435/240.26; 435/948; 435/974

[58] Field of Search ............... 435/240.2, 240.26, 5, 435/948, 974, 7.1, 7.2, 7.21, 7.24

[56] References Cited

PUBLICATIONS

Person, S. et al. 1982, Virology 117 293–306.
J. M. Keller. 1976. Virology 72 402–409.
White, J. et al. 1983. Quant. Rev. Biophys. 16 151–195.
Capone, Jr. et al. 1982. J. Biol. Chem. 257 16–19.
McIntosh, K. 1985. In: Virology. ed B. N. Fields, pp. 309–322.
K. Dahl, K. Martin and G. Miller, "Differences Among Human Immunodeficiency Virus Strains in Their Capacities to Induce Cytolysis or Persistent Infection of a Lymphoblastoid Cell Lines Immortalized by Epstein–Barr Virus", *Journal of Virology*, vol. 61, No. 4, 1602–1608, May 1987.

*Primary Examiner*—Christine M. Nucker
*Assistant Examiner*—D. R. Preston
*Attorney, Agent, or Firm*—Sprung Horn Kramer & Woods

[57] ABSTRACT

A cell line transformed by EBV and infected with a virus, e.g., HIV, which cell line does not release extracellular virus, but which forms syncytia when 1) these cells are co-cultivated with lymphocytes permissive for HIV infection and 2) antibodies to HIV are not present (syncytia formation is specifically inhibited by antibodies by HIV).

Syncytial formation induced by cell lines not producing detectable HIV provides a unique and less hazardous test for the detection of non-productive HIV infection as well as for the determination of antibody response to HIV vaccines.

5 Claims, No Drawings

EPSTEIN-BARR VIRUS TRANSFORMED CELL LINES SUPERINFECTED WITH A SECOND VIRUS

GOVERNMENT RIGHTS

This invention was made with United States government support under Grant AI 21186 from the NIH. The United States Government has certain rights in this invention.

BACKGROUND OF THE INVENTION

1. Field of the Invention

The present invention involves Epstein-Barr Virus (EBV) transformed cells which have been superinfected with a second virus and which, while expressing components of exogenous virus on their surface, do not release extracellular virus of the superinfecting strain. More particularly, the present invention relates to a cell line transformed by EBV which contains the EBV genome in a latent state; these cells superinfected by the HTLVIII strain of the human immmunodeficiency virus (HIV) give rise to a population of cells which do not release extracellular HIV, but which form syncytia when cocultivated with lymphocytes permissive for HIV. These syncytia are inhibited by antibodies to HIV.

2. Background Information

The human immunodeficiency virus is an essential element in the causation of acquired immune deficiency syndrome (AIDS). Cell to cell transmission of HIV with syncytia formation is believed to play an important role in dissemination of this virus throughout the body.

With the ever increasing number of reported AIDS cases, there is great need to more accurately determine the severity of the disease. Furthermore, there is a need to measure functional antibodies in vaccine recipients, without the use of possible infectious antigens.

K. Dahl, K. Martin and G. Miller, "Differences Among Human Immunodeficiency Virus Strains in Their Capacities To Induce Cytolysis or Persistent Infection of a Lymphoblastoid Cell Lines Immortalized by Epstein-Barr Virus", *Journal of Virology*, Vol. 61, No. 5, 1602–1608, May 1987 described the use of the X50-7 line of human umbilical cord lymphocytes immortalized by EBV and infected with HTLV-IIIB to form cell line LL58, which released extracellular HIV.

DEFINITION

Superinfection—A fresh infection added to an existing infection.

SUMMARY OF THE INVENTION

The above needs, as well as other needs, aims and other objects are satisfied by the present invention which concerns the partial expression of viruses which have superinfected EBV transformed cells. These cells, while expressing components of a specific superinfecting virus, do not release extracellular virus of the superinfecting strain, but form syncytia when cocultivated with cells permissive for infection by the superinfecting virus and in the absence of antibodies to this virus. More particularly, the present invention relates to a cell population transformed by EBV and containing the EBV genome in a latent state; these cells following superinfection, with the HTLV-IIIB strain of human immunodeficiency virus (HIV) gave rise to a population of cells which do not release extracellular HIV, but which form syncytia when they are cocultivated with cells, particularly lymphocytes, permissive for HIV. These synctia are inhibited by antibodies to HIV. Therefore this cell line can detect HIV antibodies without recourse to the use of infectious HIV antigens.

The present invention further concerns a syncytium inhibition (SI) assay using the aforementioned cell line. This assay is rapid, quantitative and reduces the biohazard of working with infectious HIV as the basis for measurement of biologically functional antibody responses.

The assay involves incubating a sample, e.g., serum, suspected of containing antibodies to a virus, e.g., HIV, with a cell line as described above and determining the presence or absence of syncytial formation.

DETAILED DESCRIPTION OF THE INVENTION

The syncytium inhibition (SI) assay of the invention can be used for samples comprising bodily fluids containing antibodies, e.g., cerebrospinal fluid, amniotic fluid, ascites fluid and serum.

Such assay can be conducted under conditions to permit antibody binding, e.g., a temperature of 25° C. to 38° C., preferably 37° C. and a time of ½ to 3 hours, preferably 1 hour.

The present invention concerns cells that are fusogenic, but are non-productively infected with a virus, e.g., HIV. The cells do not release infectious virus.

A lymphoblastoid cell line transformed by EB virus (designated X50-7) became chronically infected by HIV (HTLV IIIB strain) after initial infection with HTLV IIIB (see *J. Virol.*, 61, 1602–1608, (1987)). After about nine months this cell line (called LL58 deposited with the American Culture Collection on April 26, 1988, ATCC No. CRL 9693) stopped releasing extracellular virus as detectable by p24 antigen capture, reverse transcriptase, or infectivity assays of supernatants. Normal HIV maturation was not seen by electronmicroscopy. Nonetheless the LL58 line formed syncytia with uninfected X50-7 cells. About 1 in 5,000 LL58 cells is a syncytia former. Syncytia formation can be inhibited by human sera with antibodies to HIV (these antibodies are detected by an immunoblot assay). The syncytia inhibition test of the present invention affords a simple, rapid way to measure functional antibodies to, for example, HIV.

The present invention can be used to measure functional antibodies to a virus, e.g., HIV. This may be important in distinguishing patients with severe disease as contrasted with those with mild disease. In a preliminary study of children it was found that 8 of 8 children with mild disease (lymphocytic interstitial pneumonitis) had syncytium inhibition (SI) titers of 1:40 or greater (4 of 8 had titers of ≧1:160). Of seven children with severe AIDS and opportunistic infection five of the seven lacked detectable SI antibodies. Two of the seven children had low titers (1:20).

Another potential application of the present invention is the measurement of functional antibodies in vaccine recipients. Furthermore, the present invention can be used to test potential AIDS drugs.

The syncytia inhibition test of the present invention affords a simple, rapid way to measure functional antibodies to viral proteins expressed on the surface of EBV-transformed cells.

Besides HIV, it is expected that other enveloped viruses can infect EBV-transformed cells, potentially without subsequent release of extracellular virus. These viruses would include respiratory syncytia virus, herpes simplex virus, influenza virus, arboviruses and in fact any enveloped virus.

The invention will now be described with reference to the following non-limiting examples in which EBV-transformed cells were superinfected with HIV and in which the SI assay is shown to detect functional antibodies to HIV.

EXAMPLES

Example 1

Production of Cell Lines

Human umbilical cord lymphocytes were immortalized in vitro by EBV to produce a lymphoblastoid cell line designated as X50-7, containing latent EBV. Such cell line X50-7 was found to be highly susceptible to HIV. Cell line X50-7 contains a complete EBV genome and about 60 to 70% Of X50-7 cells bear the CD4 receptor.

An HIV-carrier line, designated as LL58 was formed by infection of X50-7 cells with the HTLV-IIIB strain of HIV (HTLV-IIIB was derived by incubation of HT cells with pooled concentrated supernatant fluids from cultured lymphocytes of several AIDS patients).

The growth medium for the cell line was RPMI 1640 with 10% fetal calf serum and antibiotics. Cells were split 1:2 or 1:3 every 4 to 7 days and maintained at 5% $CO_2$ at 37° C.

Cell line LL58 was productive of infectious virus for eight to nine months. LL58 supernatants initially contained HIV titratable to $10^{-4}$. Then because immunoblots(IB) of cell extracts showed decreased HIV expression, other assays were used to probe for HIV. These included electron microscopy(EM) and reverse transcriptase(RT), core(p24) antigen-capture(AC) and infectivity assays(INF) of supernatants using an HIV-sensitive subclone of X50-7, called X50-7.8. Immunofluorescence(FA) and IB were conducted using HIV polyvalent human antisera.

These tests revealed that cell-free virus was undetectable by RT, AC and INF. FA revealed extremely rare positive cells and IB had only a weak band of MW 27kd. EM of LL58 cells showed no extracellular virus; very rare cells showed an occasional virion which appeared intravesicular.

Example 2

Syncytia Formation and Syncytium Inhibition Assay

Following co-cultivation of LL58 with fresh X50-7.8 cells (cell line X50-7.8 was deposited with the American Type Culture Collection on Apr. 26, 1988, ATCC No. 9694), multinucleated giant cells formed after overnight incubation. The numerous syncytia formed by the co-cultivation expressed HIV by immunofluorescence and were specifically inhibited by human HIV polyvalent antisera. About 1 in 5,000 LL58 cells leads to syncytium formation (fusion), a cytopathic effect associated with HIV.

With fusion, an electron microscopy showed limited numbers of extracellular virions; longer co-cultivations (10-14 days) caused release of enough HIV to be passed from supernatants to fresh X50-7.8 cells.

A syncytium inhibition (SI) assay was developed using this system. 34 of 39 HIV antibody-positive human sera inhibited syncytium formation at dilutions of 1:20 or greater, whereas none of 17 sera lacking HIV antibody showed SI activity. In the pediatric population those patients with the highest SI antibody titers have had a more favorable clinical course.

It will be appreciated that the instant specification and claims are set forth by way of illustration and not limitation and that various modifications and changes may be made without departing from the spirit and scope of the present invention.

What is claimed is:

1. A cell line identified by ATCC No. CRL 9693, or a cell line derived from cell line ATCC No. CRL 9693.

2. A syncytium inhibition assay method for detection of antibodies to HIV virus comprising (a) incubating a sample n suspected of containing said antibodies with a cell population according to claim 1, (b) co-cultivating the cell population with EBV human transformed lymphocytes identified by ATCC No. CRL 9694, and then (c) determining the presence of absence of syncytia formation, the absence of syncytia formation indicating the presence of HIV antibodies.

3. A method according to claim 2, wherein the sample comprises an antibody-containing body fluid.

4. A method according to claim 3, wherein the antibody-containing body fluid is serum.

5. A method according to claim 2, wherein the incubation is conducted at 25° C. to 38° C. for ½ hour to 3 hours.

* * * * *

UNITED STATES PATENT AND TRADEMARK OFFICE
CERTIFICATE OF CORRECTION

PATENT NO. : 5,178,999
DATED : January 12, 1993
INVENTOR(S) : Miller et al.

It is certified that error appears in the above-identified patent and that said Letters Patent is hereby corrected as shown below:

Col. 4, line 36    After " sample " delete " n "

Signed and Sealed this

Twenty-first Day of June, 1994

Attest:

BRUCE LEHMAN

*Attesting Officer*        *Commissioner of Patents and Trademarks*